US00PP27439P3

(12) United States Plant Patent
Roe

(10) Patent No.: US PP27,439 P3
(45) Date of Patent: Dec. 6, 2016

(54) TANGERINE TREE NAMED 'C37'

(50) Latin Name: *Citrus reticulata*
Varietal Denomination: C37

(71) Applicant: Bill Roe, Eagle Lake, FL (US)

(72) Inventor: Bill Roe, Eagle Lake, FL (US)

(73) Assignee: GJH LLC, Winter Haven, FL (US)

( * ) Notice: Subject to any disclaimer, the term of this patent is extended or adjusted under 35 U.S.C. 154(b) by 93 days.

(21) Appl. No.: 14/121,775

(22) Filed: Oct. 15, 2014

(65) Prior Publication Data

US 2016/0113173 P1 Apr. 21, 2016

(51) Int. Cl.
*A01H 5/08* (2006.01)

(52) U.S. Cl.
USPC ..... Plt./201

(58) Field of Classification Search
USPC ..... Plt./201, 202
See application file for complete search history.

*Primary Examiner* — June Hwu
(74) *Attorney, Agent, or Firm* — Cassandra Bright

(57) ABSTRACT

A new and distinct *Citrus reticulata* cultivar named 'C37' is disclosed, characterized by production of large, nearly seedless fruit of beautiful internal and external color that peels very easy. Plants do not require a cross-pollinator for fruit production. The new cultivar is a *Citrus reticulata*, Tangerine tree useful for commercial fruit production.

3 Drawing Sheets

Latin name of the genus and species: *Citrus reticulata.*
Title: Tangerine Tree Named 'C37'.

BACKGROUND OF THE INVENTION

The new cultivar is a product of a planned breeding program conducted during 2000 under the direction of the inventor, Bill Roe, a citizen of the United States. The inventor no longer has record of the seed parent, the pollen parent is unknown.

This new variety was found in November 2006 in a commercial nursery in Winter Haven, Fla. Plants were first propagated by tissue culture, using embryo culture, in 2006 and subsequently grafted onto rootstocks US-897 and US-942. Development, evaluation, tissue culture and grafting all first took place at the inventor's commercial nursery in Winter Haven, Fla. USA. Subsequent evaluations of the variety have shown the characteristics to be true to type.

SUMMARY OF THE INVENTION

The cultivar 'C37' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'C37'. These characteristics in combination distinguish 'C37' as a new and distinct *Citrus reticulata* cultivar:

1. Large fruit with Moderately slick skin fruit.
2. Low seed count.
3. Very easy and dry to peel.
4. High brix and moderate acid fruit with delightful flavor.
5. Self pollinating.
6. Heavy fruiting.

7. Has a crunchy and yet juicy internal disposition with a rich juice color.

COMPARISON TO PARENT VARIEITES

Seed Parent is unknown. Plants of the new cultivar 'C37' are similar to plants of the pollen parent, *Citrus reticulata* 'Honey Tang' in most horticultural characteristics, however, plants of the new cultivar 'C37' differ in the following ways;

1. Fruit is much earlier to mature.
2. Peel color a much deeper orange.
3. Significantly fewer seeds.
4. Less oblate fruit shape.
5. Tree grows less upright.

COMMERCIAL COMPARISON

The new variety is best compared to the commercial variety, 'Tangelo,' unpatented. 'C37' is similar to 'Tangelo' in many horticultural characteristics; however, 'C37' differs in the following;

1. Much easier to peel.
2. Peels dry with very little peel oil.
3. Fruit less sensitive to plugging.
4. Internal fruit color is a deeper orange.
5. Far fewer seeds.

BRIEF DESCRIPTION OF THE PHOTOGRAPH

The accompanying photograph in FIG. 1 illustrates in full color examples of typical fruit harvested from 'C37'.

Figure 1:
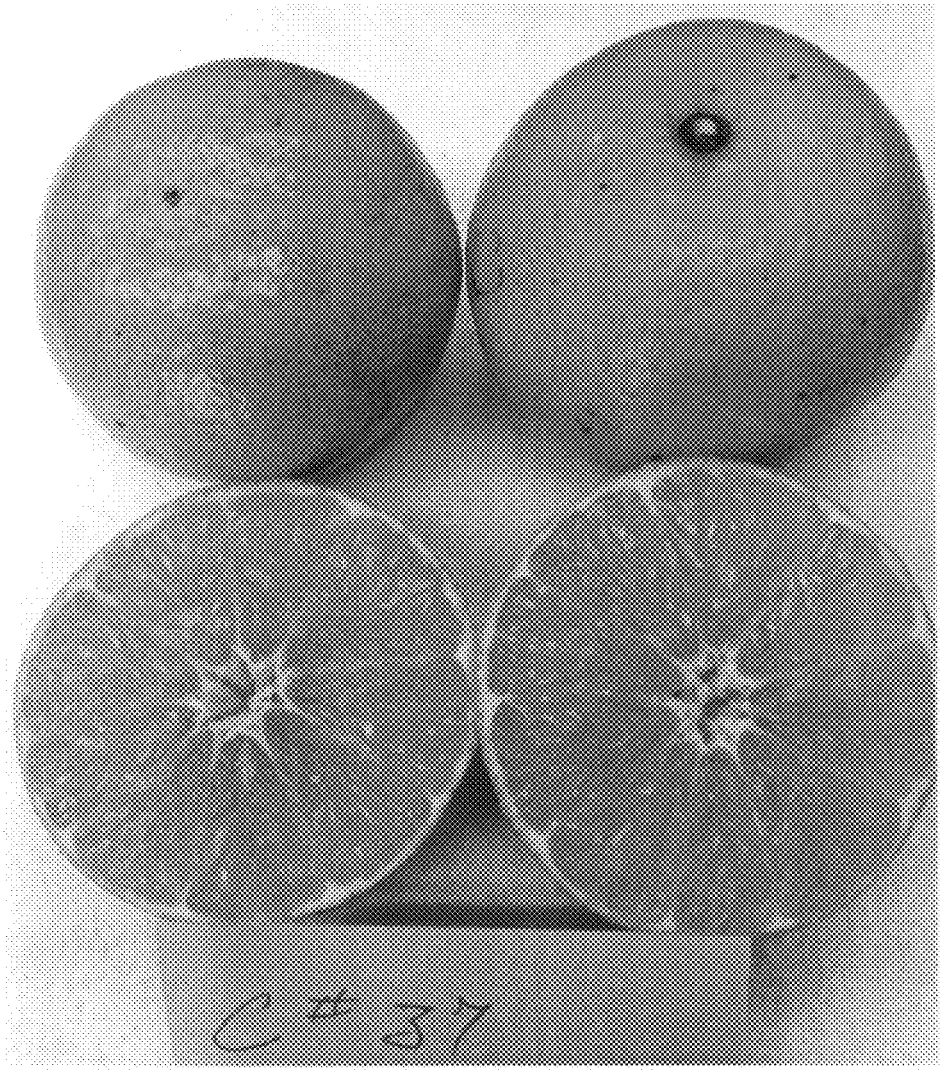
Figure 2:
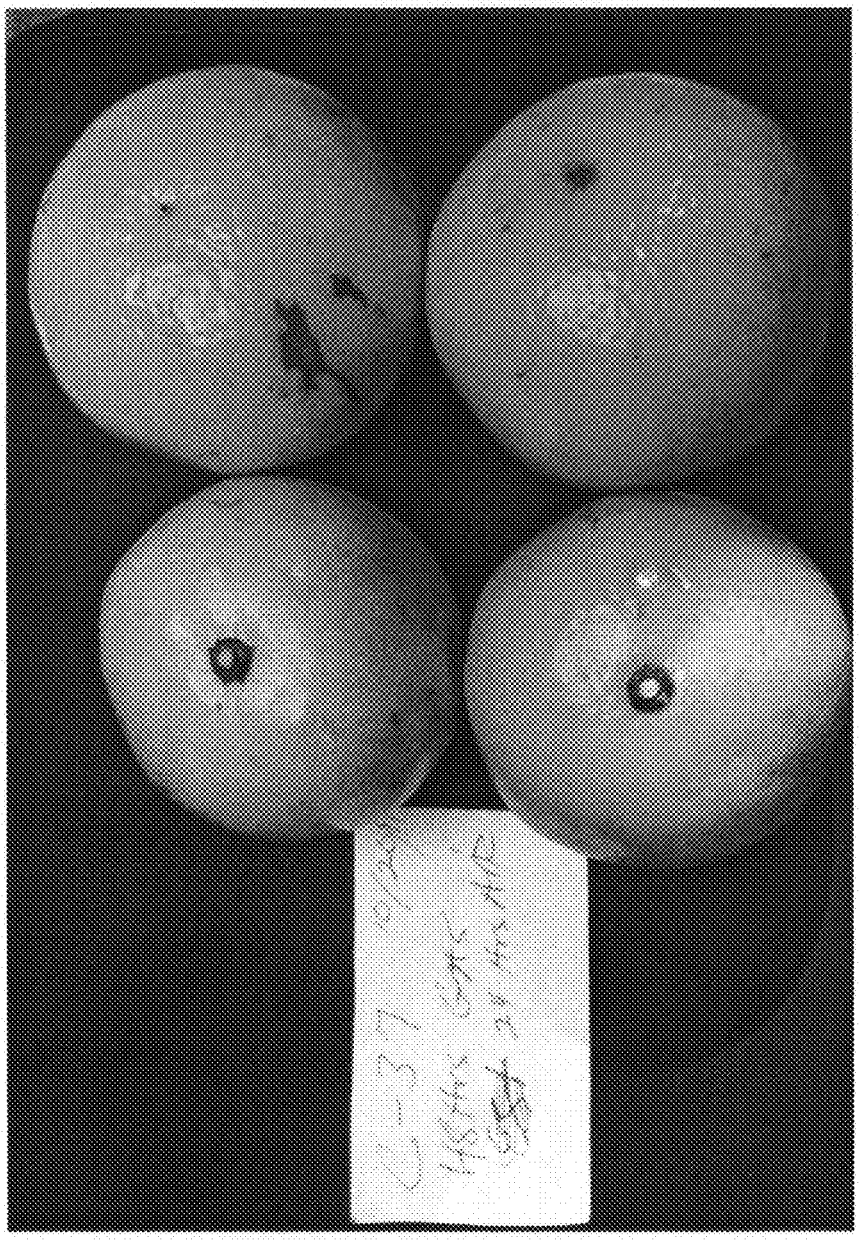
FIG. 2 illustrates in full color the exterior of the fruit, before and after treatment with ethylene gas.
Figure 3:
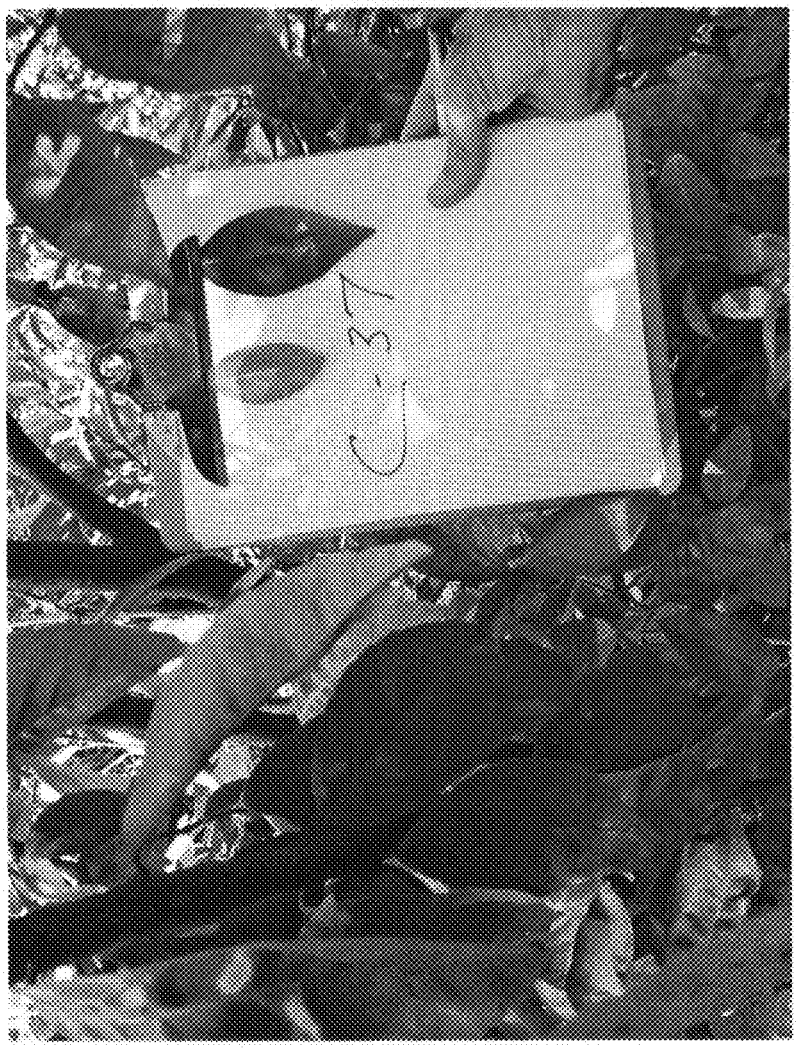
FIG. 3 illustrates branches and typical foliage of 'C37'.

Photographs are taken of plants approximately 2 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'C37' plants grown outdoors under commercial trial conditions in Winter Haven, Fla. USA. The growing temperature ranged from 10° C. to 35° C. during the day and −4° C. to 20° C. at night. Measurements and numerical values represent an average from the most typical specimens.

Botanical classification: *Citrus reticulata* 'C37'.

PROPAGATION

'C37' is typically grafted onto rootstock of *Citrus reticulata* US-897 and US-942

PLANT

Age of the plant described: Approximately 2 years.
Plant habit: Below average canopy density.
Height: Approximately 185 cm.
Growth rate: Approximately 2 years to 185 cm.
Plant spread: Wider than average row width, as the tree grows a lot of fruit on the extremity.
Vigor: Good.
Length of primary lateral branches: Approximately 40-70 cm. Average of 60 cm.
Quantity of lateral branches: 2-4, Average of 4.
Angle of lateral branches from main trunk: 150-160° degrees.
Branch diameter: 3.5-5 Average 4 cm.
Trunk texture: Smooth.
Trunk color: Near RHS Brown 200B.
Trunk diameter: Average 7 cm on a 2 year old plant.
Spines:
- *Density*.—Absent to minimal.
- *Size*.—Average length about 1.5 cm. Base approximately 0.6 cm in diameter.
- *Color*.—Near RHS Grey-Brown 199D.

FOLIAGE

Leaf:
- *Average length*.—Typical range, 7-13 cm. Average of 9-9.5 cm.
- *Average width*.—Typical range, 3.3-6 cm. Average of 4.5-4.6 cm.
- *Shape of blade*.—Elliptic.
- *Apex*.—Acute, with very small notch.
- *Base*.—Broad tapered.
- *Attachment*.—Petioled.
- *Margin*.—Entire.
- *Texture of top surface*.—Glabrous.
- *Texture of underside*.—Glabrous.
- *Aspect*.—Foliage typically somewhat upwardly folded. No twisting or blistering with normal cultural conditions.
- *Color*.—Mature foliage upper side: Near RHS Green 137A. Mature foliage under side: Near RHS Green 139C.
- *Petiole*.—Length: Range: 9.0-12.0 mm Average length 9.0-9.5 mm. Width: Average 4 mm. Pubescence: None, surfaces glabrous. Color: Upper and lower surfaces near Yellow-Green 147A.
- *Petiole wing*.—Not typically present.

FLOWER

Inflorescence and flower type and habit: Single rotate flowers emerging from leaf axils.
Flowering period: In Florida, flowering typically begins about March 10 and continues through April 5. Typical peak flowering occurs in Florida between March 15 and March 25.
Flower longevity on plant: Approximately 2 weeks.
Persistent or self-cleaning: Self-cleaning.
Bud:
- *Shape*.—A small popcorn bud that elongates to a blunt nosed cylindrical bud.
- *Length*.—Average 8-9 mm.
- *Diameter*.—Average 5 mm.
- *Color*.—Near RHS White 155A.

Flower size:
- *Diameter*.—Average 2.2-2.3 cm.
- *Depth*.—Average 1.0 cm.

Corolla/petals:
- *Arrangement*.—Rotate, fused at base.
- *Petal quantity*.—5.
- *Length*.—Average 18-10 mm.
- *Width*.—Average 2.5 to 3.0 mm.
- *Texture*.—Smooth without pubescence.
- *Apex*.—Acute.
- *Base*.—Fused.
- *Margin*.—Smooth.

Color: Petals are white upon abscission.
Calyx/sepals: Filaments separate easily.
- *Quantity per flower*.—5.
- *Shape*.—Straight.
- *Length*.—Average 6-7 mm.
- *Width*.—Average 1 mm.
- *Texture*.—Smooth.
- *Color*.—Upper Surface: Near RHS Green 137A. Lower Surface: Near RHS Green 137A.

Pedicel:
- *Length*.—Average 4-5 mm.
- *Diameter*.—Average 1 mm.
- *Color*.—Near RHS Green 137A.
- *Texture*.—Smooth without pubescence.

Fragrance: Sweet, typical *Citrus* flower scent.

REPRODUCTIVE ORGANS

Stamens:
- *Number*.—Most commonly 12.
- *Filament length*.—Approximately 2.2 cm.

Anthers:
- *Shape*.—Globular.
- *Length*.—Approximately 0.2 cm.
- *Color*.—Near RHS Yellow-White 158A.
- *Pollen*.—Color: Near RHS Yellow 8C. Quantity: Moderate.

Pistil:
- *Number*.—1.
- *Length*.—Approximately 0.8 cm.
- *Style*.—Length: 0.6 cm. Color: Near RHS Green-Yellow 1D.

*Stigma*.—Shape: linear. Color: Near RHS Yellow 8D. Ovary Color: RHS Green 143C.

FRUIT

General shape: Spherical to very slightly oblate. Not as round as 'Hamlin' or 'Valencia', but not as oblate as 'Murcott'.

*Proximal shape*.—Strongly rounded.

*Distal shape*.—Rounded.

Neck: Neck not present.

Depression, at stalk: Typically absent.

Oil glands: Almost entirely small. Moderate quantity.

Median cross section: 8 cm.

Flesh color when ripe: Between RHS Orange 26A and Orange N25A.

Brix at consumption: 11.60, on the date: Nov. 16, 2011.

Brix at harvest: 11.30. Acid 0.68 Ratio of 16.61.

Average weight: 230 grams.

Minimum weight: 170 grams.

Maximum weight: 290 grams.

Length: 62-70 mm.

Width: Range: 7-8.5 cm. Average of 8 cm.

Segment number per fruit: 9-13.

Fruit peduncle length: 80-110 mm.

Fruit peduncle width: 6 to 8 mm.

Skin/rind thickness: 20 mm.

Skin/rind texture: Mostly smooth with very small protruding oil cells.

Skin exterior coloration: Near RHS Orange N25B.

Skin interior coloration: Near RHS Yellow-Orange 23C.

Rind adherence: Weak adherence, fruit peels very easily.

Rind oil: Low quantity of oil. Inner surface oil glands conspicuous.

Albedo: Colored near Yellow-White 158D. None or almost no adherence to flesh, adheres to the peel. Very minimal to no strands.

Fruit core: Sparse density.

Rudimentary segments: Absent.

Segment wall strength: Moderate for tangerine.

Fruit juiciness: Very high.

Harvest time:

*First harvest*.—Early November.

*Last harvest*.—Month of January.

Overall cropping quantity: Above commercial averages.

Mature seed color: Near RHS Yellow-Orange 20D.

Quantity seed per fruit: 1-6 seeds per fruits with an average of 3 seeds.

Seed shape: Oval with slight tail.

Seed length: 12 to 13 mm.

Seed width: 7 to 8 mm.

Other: A large, low seed fruit that peels extremely easy and dry, with beautiful internal and external color and extremely good taste.

OTHER CHARACTERISTICS

Storage life: Storage life is a minimum of 45 plus days at 2° C.

Disease/pest resistance: Inventor has not observed resistance nor susceptibility to diseases and pests.

Other fruit features: Does not require cross pollination.

What is claimed is:

1. A new and distinct Tangerine tree named 'C37' as herein illustrated and described.

* * * * *